United States Patent
Fredenburgh et al.

(10) Patent No.: US 7,314,748 B1
(45) Date of Patent: Jan. 1, 2008

(54) ODOR CONTROL AGENT

(75) Inventors: Jeffrey Kent Fredenburgh, Stouffville (CA); Rae Anne Cordick, Toronto (CA)

(73) Assignee: Life Science TGO, S.R.L., Bridgetown (BB)

( * ) Notice: Subject to any disclaimer, the term of this patent is extended or adjusted under 35 U.S.C. 154(b) by 169 days.

(21) Appl. No.: 09/726,032

(22) Filed: Nov. 30, 2000

Related U.S. Application Data

(63) Continuation-in-part of application No. PCT/CA99/00628, filed on Jul. 13, 1999.

(30) Foreign Application Priority Data

Jul. 13, 1998 (CA) .................................. 2243011

(51) Int. Cl.
C02F 3/34 (2006.01)
C12N 1/00 (2006.01)
B09B 3/00 (2006.01)

(52) U.S. Cl. .................. 435/262.5; 435/243; 435/262; 435/822

(58) Field of Classification Search ............... 424/76.1, 424/93.4, 93.46, 93.44, 93.47, 780; 435/252.1, 435/252.4, 252.5, 253.3, 253.4, 262, 264, 435/822, 837, 829, 852
See application file for complete search history.

(56) References Cited

U.S. PATENT DOCUMENTS

| | | | |
|---|---|---|---|
| 3,720,606 A * | 3/1973 | Horney | |
| 4,680,212 A * | 7/1987 | Blyth et al. | |
| 4,839,212 A | 6/1989 | Blyth et al. | 428/96 |
| 4,925,707 A * | 5/1990 | Vinod | |
| 4,946,672 A | 8/1990 | Gibbs | 424/76.1 |
| 5,154,594 A | 10/1992 | Gamlen | 119/171 |
| 5,741,553 A | 4/1998 | Manolas et al. | 427/421 |
| 5,863,882 A * | 1/1999 | Lin | 510/397 |
| 6,265,191 B1 | 7/2001 | Mizusawa et al. | 435/177 |
| 6,325,934 B1 | 12/2001 | Tobey, Jr. et al. | 210/606 |
| 2003/0089381 A1 | 5/2003 | Manning, Jr. | 134/1 |

FOREIGN PATENT DOCUMENTS

| | | |
|---|---|---|
| EP | 0 476 915 A2 | 3/1992 |
| EP | 0 878 202 A2 | 11/1998 |
| EP | 1 096 959 B1 | 8/2003 |
| GB | 2 362 814 A | 12/2001 |
| JP | 2-121665 | 5/1990 |
| JP | 5-153971 | 6/1993 |
| JP | 7-222790 | 12/1995 |
| JP | 9-28377 | 2/1997 |
| WO | WO 96/19611 A1 | 6/1996 |
| WO | WO 97/25865 A1 | 7/1997 |
| WO | 43385 * | 11/1997 |
| WO | WO 99/46350 A1 | 6/1999 |
| WO | WO 00 03752 A | 1/2000 |
| WO | WO 00/63338 A1 | 10/2000 |
| WO | WO 02/33035 A1 | 9/2002 |
| WO | WO 03/056096 A1 | 7/2003 |
| WO | WO 03/064755 A2 | 8/2003 |

OTHER PUBLICATIONS

Database WPI, Week 199329, Derwent Publications Ltd., London, GB; AN 1993-231489.
XP002210738 Deodorise Supress Excretion Bad Smell Contain *Bacillus megaterium* Effect Range Malodorous Smell.
JP 05 153971 A (Ito Chu Techno Chem KK) Jun. 22, 1993 Abstract.
Hans G. Schegel et al., *General Microbiology*, 7th ed., p. 83 (1993).
Brochure for Bi-Chem® GC 600L.
Brochure for Bi-Chem® MSB 4X.
Brochure for Bi-Chem® Bioclean Carpet Cleaner.
Response to Summons in Opposition by Novozymes Biologicals, Inc. in European Patent No. 1 096 959 B1 with attached Declaration and Exhibits (139 pages) (Aug. 2005).

* cited by examiner

*Primary Examiner*—David M. Naff
*Assistant Examiner*—Deborah K. Ware
(74) *Attorney, Agent, or Firm*—Fitzpatrick, Cella, Harper & Scinto

(57) ABSTRACT

The present invention provides in one aspect for a method for controlling odor associated with spills of organic material which can cause odors on carpets. The method comprises applying to the carpet a preparation of dormant bacteria, which when activated are effective to control odors. The dormant bacterial preparation is allowed to become associated with the carpet, such that when the carpet is exposed to organic material which can cause odors, the bacteria are capable of becoming active and digesting the organic material. The formulation may contain other agents such as odor neutralizing or masking agents, enzymes, foaming or anti-foaming agents.

25 Claims, 5 Drawing Sheets

Scanning Electronic Microscopic
- No Bacteria Added

Scanning Electronic Microscopic Results
Fiber with Bacteria Spore Blend

ODOR CONTROL AGENT

This application is a continuation-in-part of PCT/CA99/00628 Filed Jul. 13, 1999.

FIELD OF THE INVENTION

The present invention is directed to a method of controlling odor associated with deposits on surfaces, particularly spills of organic material on surfaces, more particularly on carpet or other fibrous material and to an odor control agent for use in the method. The odor control agent can be applied to the surface, especially carpet or other fibrous material at various stages during manufacture or use. The effect of the odor control agent is long lasting.

BACKGROUND OF THE INVENTION

There are many instances where owing to deposits of organic material on surfaces, offensive odors can arise through the presence of the organic material or its decomposition. For example, much household waste contains organic material, which upon decomposition can give rise to offensive odors. This is particularly true where the household waste must be stored for a period of time prior to its disposal. Similarly, many fibrous materials utilized in household applications are also susceptible to soiling by organic based material, which can give rise to offensive odors. These fibrous materials include carpet, batting used for mattresses, pillow and pad, as well as other relatively porous surfaces encountered in the household or commercial environment.

Many fibrous materials, such as polypropylene and wool, and particularly nylon used in the manufacture of carpets, batting and household fabrics may be susceptible to staining especially from the many food dyes used in beverages and other foods as well as from other chemicals from many sources. Nylon carpet fibers are often treated with stain blockers such as a sulfonated phenol formaldehyde condensate polymer, a sulfonated naphthol formaldehyde condensate polymer, a hydrolyzed vinyl aromatic maleic anhydride polymer or combinations thereof. The stain blockers act to prevent or reduce the ability of organic dyes, particularly acid dye colorants from chemically reacting with and bonding to the nylon. The fibrous material, especially carpet fibers are also commonly coated with a fluorochemical anti-soiling agent to improve the anti-staining or anti-soiling characteristics of the carpet surface. The fluorochemicals reduce the tendency of soil to adhere to the fiber making the clean up of any spills or soil on the carpet easier. The fluorochemicals also reduce fiber wettability, making for easy clean up of liquid spills through a simple process of blotting the spill. Examples of such fluorochemicals and other stain resistant chemicals are given, for example, in U.S. Pat. Nos. 4,680,212 and 4,925,707, the disclosures of which are incorporated herein by reference. The use of the stain blockers and fluorochemicals may not provide complete stain resistance to the carpet, as some materials may still penetrate the nylon fibers or react with the fibers, especially if left in contact with the carpet for extended periods of time. This may be especially true where the carpet is exposed to conditions such as direct sunlight or other UV sources or high traffic areas, as these conditions may cause the effectiveness of the fluorochemical and stain blocker coatings to be diminished.

In addition, especially in residential locations, the possibility of deposits of organic matter such as feces or urine from babies and pets can result in not only soiling of fibrous and other porous materials such as carpets and bedding but also a lingering odor and may, in extreme cases, require the replacement of the soiled object. In the past, various chemical compounds have been proposed to aid in removing odor in a cleaning process. Such chemicals generally act as odor inhibiting agents although U.S. Pat. No. 4,946,672 describes the use of biguanidine polymer compositions as odor inhibiting agents. However, even in those cases where the deposit is cleaned up and odor inhibiting agents utilized, the odor from such deposits may remain in the soiled objects and may become apparent as the effect of the odor masking agents wear off.

Deposits of various materials on carpet and other fibrous materials may also give rise to other concerns. Many of the deposit materials are capable of supporting bacterial growth, especially in the case of feces which contains many bacteria. Some of the bacteria that may grow, as a result of a deposit, may have the potential of causing disease in persons exposed to them, such as mold and mildew. Carpet and other fibrous material are also known to contain a number of naturally occurring bacteria and other organisms. Some of these bacteria may themselves give rise to odor due to incomplete digestion of organic material. There have been attempts to reduce the presence and number of bacteria present in carpet by utilizing various anti-microbial agents such as described in U.S. Pat. Nos. 4,110,504 and 5,024,840. These agents are applied to carpet in a manner similar to the way stain blockers are applied to carpet. The use of anti-microbials, while reducing the number of bacteria associated with carpet, may raise other concerns such as the potential that some of the bacteria may become resistant to effects of the anti-microbials.

Many bacterial and fungal genera are known for use in odor control due to their capability for producing enzymes that are capable of breaking down organic material. Such bacteria are particularly useful where the organic material, if allowed to remain, will give rise to malodors. Several such bacterial and fungal genera such as *Bacillus, Lactobacillus, Enterobacter, Streptococcus, Rhizopus, Nitrosomonas, Nitrobacter, Pseudomonas, Alcaligens* and *Klebsiella*, among others, are known for use in such applications with *Bacillus* sp. being the most prevalent in use in various applications.

For example, European Patent Application No. 732,396 describes the use of *Bacillus* sp. for odor control of feedstuffs used in farming and JP Patent Application No. 7-031,668 describes their use for odor control of toilets, shoe boxes and pet litter. Other uses of the *Bacillus* for odor control for baby diapers and wallpaper are described in JP Patent Application Nos. 2-121,665 and 3-059,199 respectively. Preparations of sporulated *Bacillus* in a form suitable for spraying or otherwise distributing on a deposit, especially of pet urine and feces, on a carpet for controlling odor are presently marketed by The Bramton Company of Dallas, Tex. under the trademark OUTRIGHT. The bacterial preparations are used to deodorize a deposit by application directly on the deposit. Once the deposit is deodorized, the bacteria are depleted from the site or disposed of along with the deodorized material. In the event of a new deposit on the carpet, the treatment must be repeated.

There thus remains a need for a means for treating surfaces, particularly carpet and other fibrous material to counteract the effects of deposits and especially for controlling odor associated with the deposits, particularly deposited organic material, where the effects of the odor control are preventative and long lasting.

SUMMARY OF THE INVENTION

The present invention provides in one aspect for a method for controlling odor associated with deposits of organic odor causing material in contact with a surface. The method comprises applying to the surface a preparation of dormant bacteria, which, when activated, is effective to control odors, and one or more adhering agents to allow the dormant bacterial preparation to become associated with the surface. When the surface is subsequently exposed to organic material that can cause odors, the bacteria associated with the surface are capable of becoming active and digesting the organic material.

In another aspect of the invention there is provided a composition for treating a surface, particularly a fabric or fibrous material to provide control of odor associated with deposits of organic odor causing material on the surface. The composition comprises one or more strains of dormant bacteria, which when activated are effective to control odors and one or more adhering agents.

In yet another aspect of the invention, the composition also includes an odor controlling material, preferably a molecular sieve and/or a carbonate such as sodium bicarbonate.

BRIEF DESCRIPTION OF THE DRAWINGS

Preferred embodiments of the invention are shown in the drawings, wherein.

DETAILED DESCRIPTION OF THE PREFERRED EMBODIMENTS

Figure 1A:
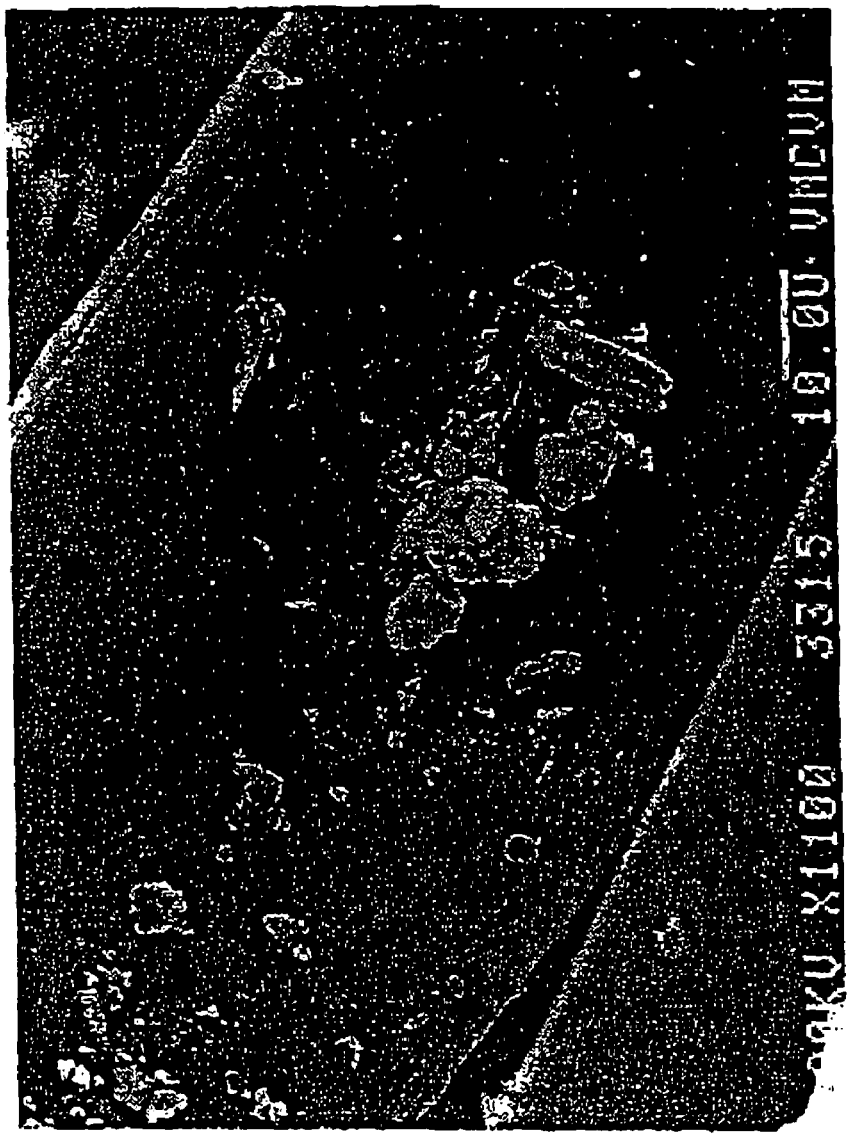
FIG. 1 illustrates scanning electron microscope pictures of carpet fibers containing no innoculum (FIG. 1A) and carpet fibers inoculated with a preferred bacterial spore blend prepared according to Example 1 of the present invention (FIG. 1B)
Figure 1B:
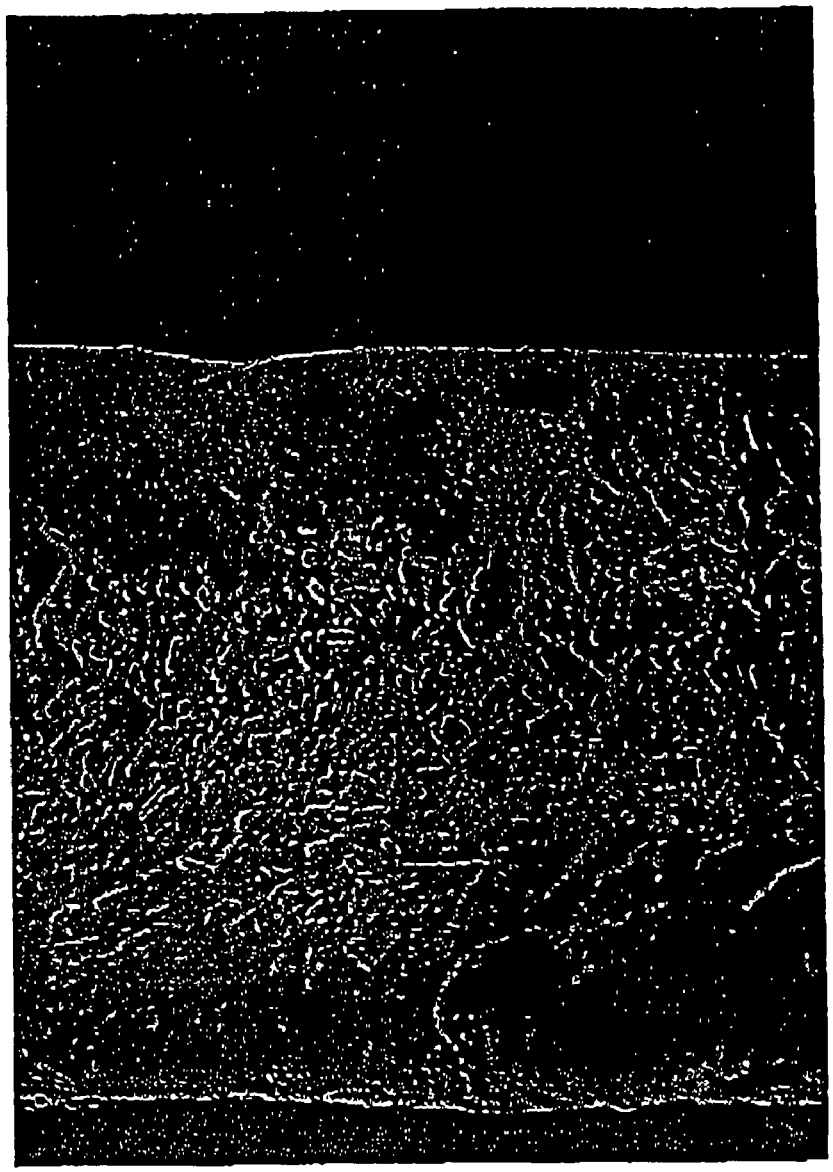
Figure 2:
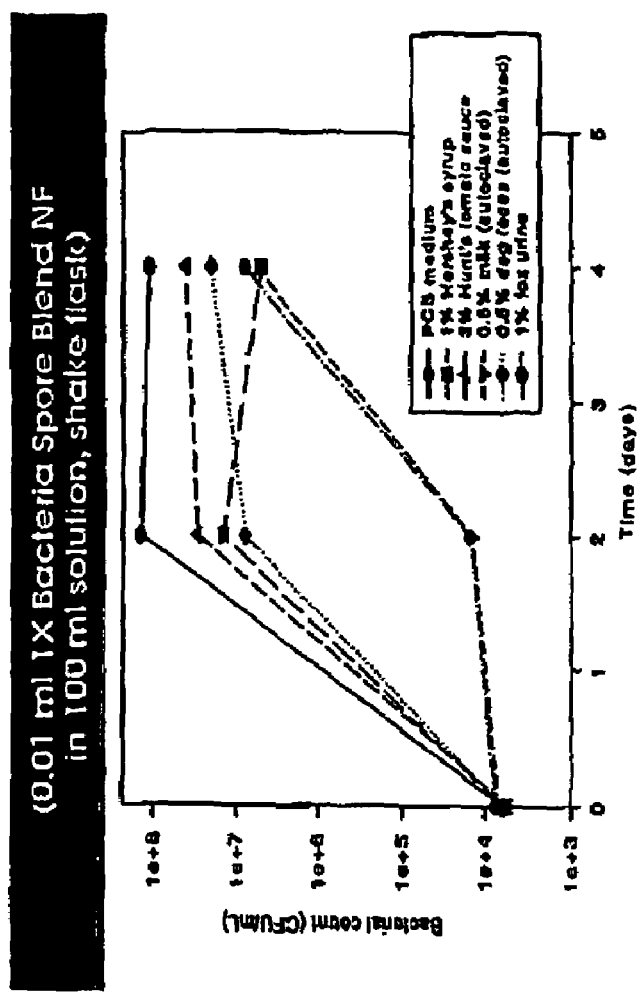
FIG. 2 is a graph illustrating the germination and growth of the bacteria spore blend on various organic soils.
Figure 3:
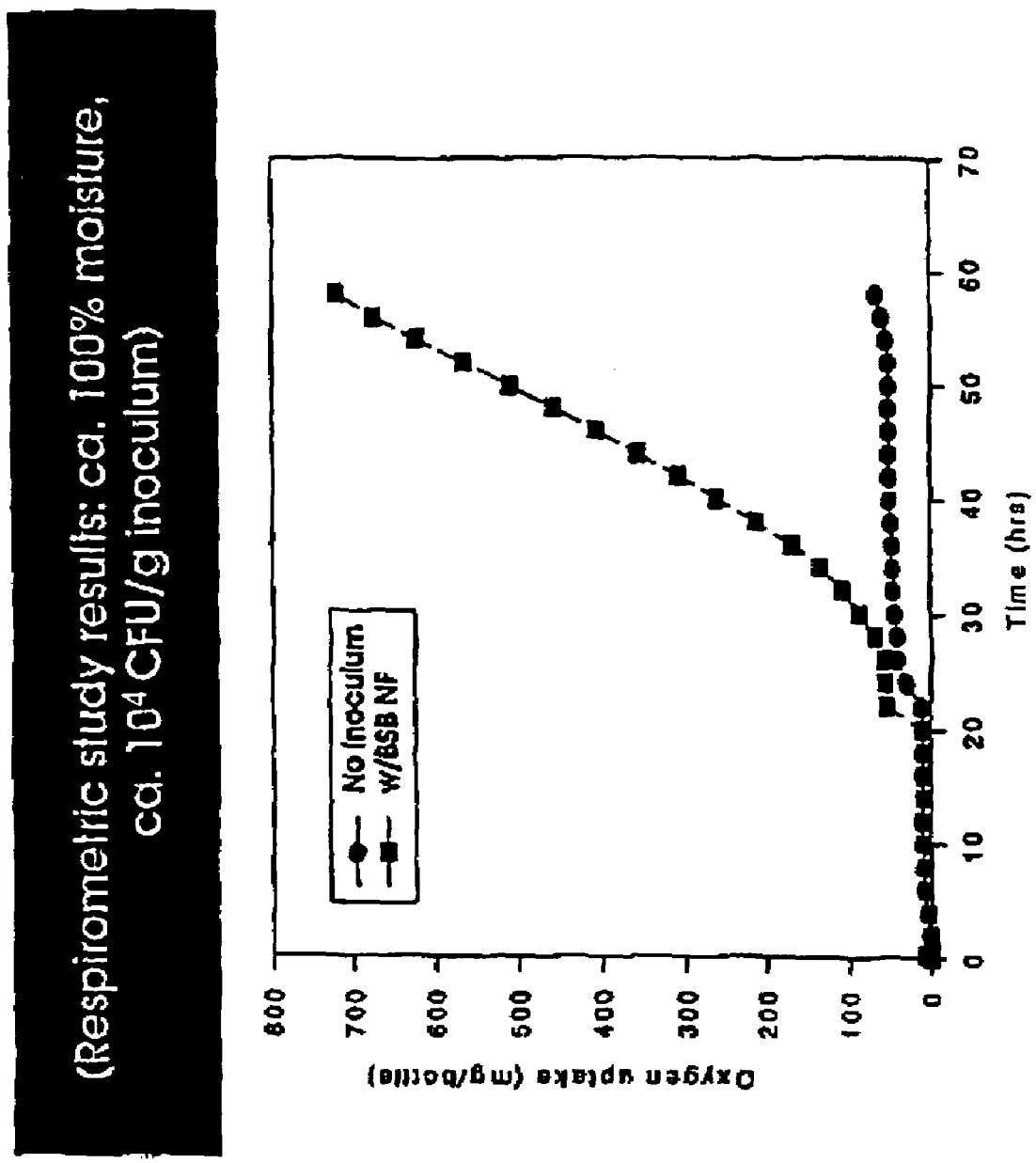
FIG. 3 is a graph illustrating the germination and growth of the bacterial spore blend in nylon carpet containing plate count broth.

The present invention is directed in one aspect to a method of controlling odor associated with deposits, particularly spills, of organic material which can cause odors on surfaces particularly carpet or other fibrous materials. The present invention is also directed to the compositions useful for preparing surfaces, particularly carpet or other fibrous material to make them capable of controlling odor as well as to the surfaces, particularly the carpet or other fibrous material so prepared. In addition to controlling odor, the compositions may also aid in reducing the staining effects of organic material.

Many bacterial genera are known to produce enzymes that are capable of breaking down organic material. Such bacteria are particularly useful where the organic material, if allowed to remain, will give rise to malodors. Several such bacterial genera such as *Bacillus, Lactobacillus, Enterobacter, Streptococcus, Nitrosomonas, Nitrobacter, Pseudomonas, Alcaligens* and *Klebsiella* amongst others are known for use in such applications, with *Bacillus* and *Lactobacillus* sp. being the most prevalent in use in various applications. Strains of bacteria from any of the above noted genera are useful in practicing the present invention. Preferably, the bacterial preparation for use in the present invention is one or more strains of *Bacillus* or *Lactobacillus*. More preferably, the strains of bacteria for use in the present invention are selected from *Bacillus licheniformis, Bacillus pasteurii, Bacillus laevolacticus, Bacillus megaterium* and *Bacillus amyloliquefaciens*. Each of these species has characteristics that make them most effective against particular types of organic materials. All of these species are capable of enhanced anaerobic and aerobic growth, *Bacillus pasteurii* is known for superior lipase production, while *Bacillus laevolacticus* has a very fast germination cycle. *Bacillus amyloliquefaciens* is high in production of protease enzymes.

The selection of the strains of bacteria for use in the present invention may depend upon many factors. One such factor is the nature of the organic material most commonly expected for the particular application. For example, in a commercial application, the most commonly expected deposits would be soil tracked in from out-of-doors, beverages such as coffee, tea, other food and the like, especially in a restaurant environment, and possibly, inks or toners for printers and other office equipment. Many of these materials are high in fatty components so the bacterial preparation may be enhanced for strains having high activity against such materials. One example of such a bacteria is *Bacillus pasteurii* known for superior lipase production. In a residential environment, the nature of the deposits may differ with out-of-doors soils. Beverages, food and urine and feces from pets and children being most commonly encountered. Depending upon the nature of the deposited material, the preparation may be selected to contain strains having enhanced activity against such materials. Another factor that may affect the nature of the deposit is the geographical location of the surface being treated. This factor would especially relate to the nature of deposits of out-of-doors soil and to the nature of food deposits. Different regions are known to have different soil types and different regions may also have differences in the foods commonly consumed due to cultural and environmental factors. In addition, the temperature of the carpet to be treated will influence the activity of the bacteria. Depending on the strain selected the bacteria will tend to exhibit enhanced activity at higher temperatures. At lower ambient temperatures, more active strains may be desired.

The bacterial preparation will typically comprise one or more strains selected from the genera and species described above. When utilizing a mixture of more than one strain, each of the individual strains may comprise between 3% and 97% of the total of the bacteria present in the preparation. Depending upon the bacteria, these percentages are based on the total cell number or colony forming units or the total mass of the bacterial preparation. For the *Bacillus* sp. the percentages are based on total cell number. Preferably, each of the strains is present in sufficient numbers to make up 10% to 70% of the total bacteria in the preparation. When mixtures of more than two strains are employed, each of the strains is most preferably present in an amount of from 20% to 40% of the total bacteria in the preparation. Particularly preferred preparations for general use in almost all applications are as follows:

| | % of total bacteria | | |
|---|---|---|---|
| Species | Range | Preferred Range | Most Preferred |
| Bacillus meqaterium | 5-60 | 20-60 | 40 |
| Bacillus pasteurii | 10-40 | 10-30 | 20 |
| Bacillus laevolacticus | 10-40 | 10-30 | 20 |
| Bacillus amyloliquefaciens | 10-40 | 10-30 | 20 |

In a preferred embodiment of the present invention an effective amount of a bacterial composition comprising one or more strains selected from the group consisting of *Bacillus megaterium, Bacillus pasteurii, Bacillus laevolacticus* and *Bacillus amyloliquefaciens* and combinations thereof are provided in a state in which the composition may be applied to a surface, such as carpet fiber or other fibrous material. The effective amount is a sufficient number of bacteria to provide a relatively uniform coverage of the surface such that when any portion of the surface is exposed to a deposit of an odor causing organic material, the bacteria will undergo rapid growth and consume the odor causing material. The factors that can affect the number of bacteria to be used relate in most part to the nature of the surface to be protected. For carpet, such factors include the nature of the fiber in terms of the material, e.g. nylon or polypropylene and the like, the characteristics of the yarn in the terms of the denier and number of filaments and the characteristics of the fiber in terms of the number of yarns and the twist. These factors relate to the nature of the carpet in terms of the weight (oz) or (g) and height of the pile. All of these factors will affect the amount of exposed surface of the fibers that might be covered by the bacterial preparation. For most applications on carpet, between about $10^6$ and $10^8$ cells per square inch of carpet fiber having a weight between about 20 oz and 40 oz is most effective with about $10^7$ cells per square inch of carpet being most preferred.

The preparations are preferably provided as a aqueous preparation of a suspension of the *Bacillus* species and one or more adhering agents in a suitable aqueous carrier, such as in distilled water, tap water, a saline solution or other such aqueous solutions.

The adhering agents are utilized to keep the bacteria associated with the surface, so that the bacteria remain associated with the surface during the normal usage of the surface. The adhering agent binds the bacteria to the surface in a manner to allow it to remain associated with the surface while also allowing the bacteria to be exposed so the dormant bacteria may be activated upon an exposure to the organic odor causing material. The nature of the adhering agent is selected based upon the surface to be treated. For fine fibrous material such as batten, the adhering agent is preferably an anti-soil fluorochemical or an acrylic polymer especially an acrylic co-polymer. For carpet and other fibers, the adhering agent is preferably, a stain blocker, an anti-soil fluorochemical, styrene butadiene rubber, nitrile rubber or polyvinyl chloride, most preferably a stain blocker or an anti-soil fluorochemical. For plastic film, the adhering agent is preferably a stain blocker, an anti-soil fluorochemical, styrene butadiene rubber, nitrile rubber, an acrylic polymer or polyvinyl chloride, most preferably a stain blocker, an anti-soil fluorochemical or an acrylic polymer. For other hard surfaces such as plastics, ceramics, tile, walls, wood, etc., the adhering agent is preferably an acrylic polymer.

The amount of the adhering agent utilized in the composition depends upon the nature of the surface to be treated, as well as the nature of the adhering agent. For relatively absorbent surfaces, such as fabrics, the concentration of the adhering agents would be greater than if the surface was less absorbent. Ideally, the amount of the adhering agent is selected to provide a film coating on the surface containing the bacteria with the thickness of the film being such to keep the bacteria associated with the surface, while allowing the bacteria to be easily exposed to any organic material with which the surface may come in contact. For most adhering agents, they will be present in an amount of between 0.01 and 20 weight percent based upon the total weight of the composition, more preferably between 0.1 and 15 weight percent, most preferably between 5 and 10 weight percent.

Most preferably, the aqueous composition comprises the odor controlling dormant bacterial strain or strains and an effective amount of a stain blocker as the adhering agent. The stain blocker is preferably selected from the group consisting of sulfonated phenol formaldehyde condensate polymer, a sulfonated naphthol formaldehyde condensate polymer, a hydrolyzed vinyl aromatic maleic anhydride polymer or combinations thereof. The aqueous composition may also include one or more fluorochemicals typically utilized for carpet treatment, as an adhering agent either on their own or in combination with the stain blocker. Examples of such fluorochemicals include products sold under the trademarks STAINMASTER, STAINMASTER with TEFLON, and ZONYL by DuPont and SCOTCHGARD by 3M.

The selection of the suitable fluorochemicals and stain-blocker is well within the knowledge of those of skill in the art. Preferably, the fluorochemicals and stainblockers selected are soluble in water, particularly when the composition is to be used on an existing surface such as installed carpet. When utilized during the manufacture of the material surface such as carpet, the fluorochemicals and stainblocker may be non-water soluble, provided as a dispersant preparation in which the elevated temperatures during the manufacturing process are used to bind the fluorochemicals and stainblocker to the carpet fiber and affix or attach the bacteria in the process. The use of the stain blocker and/or fluorochemical as adhering agent in the preparation improves the ability of the spores to become associated with the fibers. This provides increased protection of the bacteria from subsequent removal by vacuuming the possible adverse effects of environmental factors. The adhering agent, such as stain blocker and/or fluorochemical have been demonstrated to provide a protective encapsulation of the bacteria to aid in the protection of the bacteria from exposure to potentially harmful conditions such as traffic or the effects of cleaning.

The amount of the stain blocker and/or fluorochemical used in the preparations of the present invention are the amounts typically employed in the carpet and fabric industry and would be well known to those skilled in the art. Ordinarily, depending upon the nature of the stain blocker or fluorochemical and the material being treated and its location, the agents are applied to the material in an amount to result in a treatment rate of about 0.1 wt % to about 20 wt % based upon the weight of the nylon or other fibrous material being treated and the amount of stain blocker and/or fluorochemical. Commonly, the treatment rate will be from about 0.15 wt % to about 10 wt %, preferably from about 0.2 wt % to about 4 wt %, more preferably from about 0.25 wt % to about 2 wt %. Most preferably, the stain blocker or fluorochemical is applied to give a treat rate of about 0.25 wt % to 1.0 wt % based upon the weight of the nylon or other fibrous material being treated.

The odor controlling bacterial composition of the present invention they also include odor controlling materials which act to neutralize or trap odor causing material allowing time for the bacteria in the preparation to decompose the odor causing material. The odor controlling material preferably are one or more of carbonates, such as sodium bicarbonate and molecular sieves, such as silica or activated charcoal. These odor controlling materials will generally be utilized in the preparations at a concentrations typically employed for their odor controlling properties. For activated charcoal, this amount could be as much as 80 weight percent of the total weight of a concentrated formulation for use in a manufacturing process for manufacturing of the treated surface. Typically, the activated charcoal would be utilized in such applications at a concentration of between about 20 weight percent and 60 weight percent based upon the total weight of the manufacturing formulation. For the other odor controlling materials, they will typically be present in amounts of between about 0.001 and 10 weight percent based upon the weight of the total preparation, although higher percentages may also be employed. Preferably, these odor controlling materials will be present in a concentration of about 0.01-5% wt. more preferably in a concentration of about 1-2% wt. based upon the weight of the total preparation. The molecular sieves utilized in the preparations of the present inventions preferably will have a high absorbent capacity with a large surface area to volume ratio. More preferably, the molecular sieve will be selected to have a relatively uniform pore size to allow for the entrapment of the odor causing material, while at the same time preventing the bacterial cells from entering the molecular sieve. Groups of such molecular sieves are those available from UOP under the trademark ABSENCE and MOLSIV. These molecular sieves are crystalline sieves having a defined three-dimensional structure with precise pore size.

The bacteria and particularly *Bacillus* species are provided as dormant cells. The term "dormant cells" is intended to encompass cells which are in a state which are required to be activated before they can undergo growth. One example of a dormant cell is a sporulated form of the bacteria where the spores must undergo activation and germination before growth of the bacteria can occur.

As noted above, due to the protective effects of the adhering agent, particularly the stain blocker and/or fluorochemical, the active bacteria would be protected from the possible effects of environmental factors. By providing the bacteria in a dormant or sporulated form, the bacteria are further protected from environmental factors which may prove detrimental to active bacterial cells. These environmental factors may include low moisture or humidity, as the surface such as a carpet or other fibrous material would generally be kept in a dry state. Other factors may include exposure to heat, chemical agents, and UV radiation from sunlight as well as the exposure to air for those strains that may be predominantly anaerobic.

The sporulated or dormant strains of bacteria become activated and undergo germination in response to being exposed to organic material including organic material that can cause odors. The factors that promote the activation of the dormant or sporulated bacteria include the moisture and various organic compounds present in the deposit of organic material. Once activated, the bacteria undergo growth and replication, consuming the organic material in the deposit until the material is consumed. After the material is consumed, the bacteria will then become dormant by undergoing sporulation to await exposure to another deposit of organic material. It is thought that the bacteria will also be somewhat cannibalistic, in that as the bacteria break down after the depletion of the organic material, the degradation products of the break down would be utilized as a food source by other of the bacteria. Once the potential energy source is reduced and the number of bacteria is also reduced, it is thought that the remaining bacteria undergo sporulation to return to a dormant state.

The odor controlling bacterial composition of the present invention may be provided with other active ingredients depending upon the application or surface to be treated. One such additional ingredient that is preferably included in the composition of the present invention is an anti-foaming agent for reducing surface tension for reduced absorbent surfaces. The anti-foaming agent may be any commonly utilized anti-foaming agent which would be suitable for the surface to be treated. One example of such an anti-foaming agent is a silicone based anti-foaming agent, which may be utilized in compositions utilized for treating reduced absorbent surfaces, such as hard surfaces. The anti-foaming agent may also be used in compositions which are utilized in a spray bottle for direct application by the consumer, particularly for carpet or other fibrous material.

Another additional ingredient which may be utilized in the composition depending upon the application is a foaming agent for producing a foam composition for treating relatively absorbent surfaces, such as carpet. This foaming agent is preferably a lauryl sulphate, more preferably an ammonium lauryl sulphate or sodium lauryl sulphate, most preferably sodium lauryl sulphate, the foaming agent is utilized to produce a composition which can be applied to the surfaces of higher absorbency to allow the composition to be worked into the surface. This may be of particular use for treating carpet. The additional ingredients would be utilized in the compositions at the usually employed concentrations, generally 5 percent by weight or less based upon the total weight of the composition.

For treatment of most surfaces by spraying or dipping, the aqueous odor controlling bacterial composition of the present invention are preferably formulated to have the following composition:

| | Range (grams) | |
|---|---|---|
| bacteria spore blend | 61.100 to 101.047 | |
| fluorochemical | 0.05 to 20.000 | |
| sodium bicarbonate | 0.001 to 10.000 | |
| molecular sieve | 0.001 to 10.000 | |
| antifoamer | 0.001 to 5.000 | adjust as necessary |
| acidic acid | 0.001 to 5.000 | adjust ph as necessary |

More preferably, the compositions of the present invention will be as follows:

| | Range (grams) | |
|---|---|---|
| bacteria spore blend | 75.000 to 95.000 | |
| fluorochemical | 0.10 to 15.000 | |
| sodium bicarbonate | 0.01 to 5.000 | |
| molecular sieve | 0.01 to 5.000 | |
| antifoamer | 0.01 to 5.000 | adjust as necessary |
| acidic acid | 0.01 to 5.000 | adjust ph as necessary |

A particularly preferred composition according to the present invention is as follows:

| | Grams | Solids |
|---|---|---|
| bacteria spore blend | 90 | 89.02% |
| fluorochemical | 10 | 9.89% |
| sodium bicarbonate | 0.1 | 0.10% |
| molecular sieve | 0.01 | 0.01% |
| antifoamer | 0.5 | 0.49% |
| acidic acid | 0.5 | 0.49% |
| Total | 101.5 | 100.0% |

For application of the composition during the manufacturing of surfaces, the bacterial preparation may be provided as a concentrate to be diluted with the adhering agent such as the stain blocker and/or fluorochemical formulation and optionally the sodium bicarbonate and/or molecular sieve prior to application in the process for manufacturing the surface. If provided as a concentrate, the concentrate may include other agents for improving viability of the bacterial preparation. The concentrate preferably contains between 10 and 20 times the number of cells or spores per ml of compositions used in post manufacturing applications. To prepare the preparation used in manufacturing processes for surfaces, 90 to 95% by volume of the concentrate is mixed with 5% to 10% by volume of the adhering agent, particularly the stain blocker and/or fluorochemical formulation. Thus, each ml of the stain blocker and/or fluorochemical formulation is mixed with 10 to 20 ml of the concentrate to prepare the bacterial preparation for application to surfaces such as plastic film, carpet and other fibrous material during the process of manufacturing the surfaces.

As described below, for formulations used in post manufacturing application, the above formulation is diluted 1 to 10 or 1 to 20 with water or other aqueous carriers to produce a preparation which may be directly applied to installed surfaces, for example, installed carpet.

When treating surfaces such as carpet, the aqueous odor controlling bacterial composition may be applied to the surface at any stage during its manufacture. For example, when used to treat carpet, the composition may be utilized to treat the precursor filaments, yarns or fibers prior to their use in the conventional manufacturing process. The filament or yarn may be run through a bath containing the aqueous solution of the bacterial preparation or the bacterial preparation may be sprayed on the filament. After the treatment, the filaments or yarns are dried and then further processed into carpet in the normal manner. Alternatively, the carpet during the manufacturing process may be immersed, sprayed or otherwise treated with the aqueous composition. The carpet fibers may be sprayed or otherwise treated with the bacterial preparation prior to being inserted into the primary backing. Alternatively, the fibers may also be treated once they have been inserted into the primary backing, either before or after the backing adhesive and secondary backing material have been applied. The composition may also be applied to the finished carpet as a final step prior to drying and rolling. The carpet would be sprayed or otherwise treated with the aqueous bacterial preparation, after which time the carpet would be dried in the usual manner and rolled onto the roll. In the above processes the manufacturing strength preparation is preferably applied at a concentration of 1 to 10 grams per square meter of surface to result in about $5\times10^5$ to $2\times10^6$ bacteria spores per square centimeter of the treated surface.

Another option would be to apply the composition to an installed carpet either by way of a concentrated preparation such as is used in a manufacturing process or a diluted consumer strength formulation. The diluted consumer strength formulation preferably includes other agents such as enzymes, molecular sieves, sodium bicarbonate, and masking agents in addition to the bacteria spore blend and adhering agent. These other agents are generally present in the composition at concentrations normally employed for their function. When applying the composition to an installed carpet, it is not essential, but preferred that the composition be applied thoroughly and evenly throughout the length of the pile, especially reaching down to the base of the pile fiber. This is generally achieved by applying an aqueous foaming bacterial preparation to the carpet and then working the fibers to improve the contact, distribution and penetration of the bacterial preparation. This is most commonly achieved by use of a pile brush operated either by hand or automatically for example, utilizing a cleaning device such as is commonly available commercially. To enhance the penetration of the bacterial preparation, the fibers of the carpet may initially be wetted through an application of a detergent solution. This is most commonly applied where the installed carpet is cleaned using a cleaning machine prior to the application of the bacterial preparation. While the carpet fibers are still moist, the bacterial preparation may be applied and worked into the carpet, utilizing the pile brush. Once the carpet has been so treated, it is dried, either by allowing it to dry in the air at ambient temperature or through the use of hot air blown through the pile of the carpet to increase the speed of drying of the carpet. Depending upon the state of the carpet or other fibrous material, the composition may be applied in many different ways. The composition may be applied by dipping the material in the composition or by spraying the composition onto the fibrous material. In any of these cases, once the fiber or carpet is treated with the composition the treated carpet material is allowed to dry by way of applied heat or simply by ambient drying. Alternatively, or in addition to treating the carpet fiber with the aqueous composition, the carpet backing and/or carpet cushion underlayment may also be treated with the bacterial preparation. Once again, the carpet backing and/or carpet cushion underlayment may be treated during the manufacturing process, or prior to its installation. The carpet cushion underlayment may also be similarly treated during the installation of the carpet cushion underlayment.

In addition to treatment of carpets, other fibrous materials may be treated in a similar manner. For example, batting used in the manufacture of mattresses and pillows and pads, may be treated by spraying or dipping the precursor filament yarns or fibers prior to their use in the manufacture of the batting. Alternatively, the sheets of batting after their manufacture may be sprayed or dipped or otherwise treated with the aqueous odor controlling bacterial composition according to the present invention.

The aqueous odor controlling composition of the present invention may be utilized on other surfaces that would be expected to come in contact with odor causing material. Examples of such surfaces include garbage bags, shoe insoles, etc. When treating such material, the odor controlling bacterial composition of the present invention may be applied by any method which allows the surface to be treated with the preparation. For example, the surface may be sprayed or dipped or the preparation may be applied to the surface using a roller system such as a gravure roller system.

For plastic film, the preparation is preferably incorporated during the quenching bath through which the film is dipped after extrusion. It has been found that the presence of the adhering agent such as the fluorochemical in the composition acts to adhere the composition to the surface of the plastic film. Once the surface of the film has been so treated they may be utilized in the manufacturing process for producing products such as garbage bags or applied to other products such as carpet underlayment by laminating the film to the product.

The following examples illustrate the use of the present invention but are not to be construed as limiting the scope of the present invention.

Example 1

A known weight of carpet was conditioned at 50% humidity at 75° F. After conditioning, the carpet was sprayed with a suspension of a mixture of sporulated forms of *Bacillus* sp. having the following formulation:

| Species | % of total bacteria |
|---|---|
| *Bacillus licheniformis* | 40 |
| *Bacillus pasteurii* | 20 |
| *Bacillus laevolacticus* | 20 |
| *Bacillus amyloliquefaciens* | 20 |

The bacterial suspension was prepared in an aqueous solution of 5% ZONYL 7044 fluorochemical in distilled water at a concentration of $10^8$ spores per ml. The bacterial suspension was applied to the carpet in an aerosol form to provide a treatment rate of $10^7$ spores per square inch of carpet. After the application of the bacterial suspension, the carpet was dried at 290° F. in an oven in a humidity-controlled chamber for 20 minutes. A sample of the carpet fiber treated with the bacterial suspension was compared with a sample of untreated carpet fiber by scanning electron microscopy. The results of this comparison are shown in FIG. 1 where FIG. 1*a* illustrates the carpet fiber containing naturally occurring bacteria and other microorganisms adhered to the carpet fiber that was not treated. FIG. 1*b* illustrates a carpet fiber inoculated with the bacterial spore preparation. As can be seen in the micrographs, the treated carpet fiber has a large number of *Bacillus* spores adhered to the surface of the fiber with very little, if any naturally occurring bacteria or other microorganisms present in the sample.

Example 2

Samples of carpet fiber and plate count broth were examined for oxygen uptake using a standard respirometric study. Oxygen uptake is commonly utilized in those applications where it is not possible to easily measure bacterial growth by other methods. It is known that for aerobic bacteria, oxygen uptake is directly proportional to bacteria count, with the greater the uptake, the higher the corresponding bacteria count would be. The respirometric studies were conducted using a Challenge AER100 respirometer with all samples incubated under controlled temperature conditions. The treatment reactors were 500 ml bottles with $CO_2$ adsorption trap inserts containing 5 ml of 30% KOH (w/v) with alizarin yellow pH indicator. The sterilized traps were filled with the KOH caustic solution then inserted into the sterilized reactors using aseptic techniques. The $CO_2$ traps also contained sterilized medical cotton rolls used as wicks to increase the surface area of the caustic solution. Each reactor was provided with sufficient carpet material to yield 5 grams of carpet fiber. A plate count broth prepared by mixing 17 g Difco Plate Count Broth, 0.073 g $KH_2PO_4$, 0.114 g $K_2HPO_4$ per liter of distilled water and the pH adjusted to 7 was added to the reactor and the reactors autoclaved to sterilize them. The reactors were allowed to cool and 0.5 ml of the bacterial suspension utilized in Example 1 containing $10^8$ spores per ml was added to the test reactors. The same volume of distilled water was added to the control reactors. The reactors were capped without the caustic traps and rolled and swirled to ensure that the water and bacterial preparations were mixed well with the organic materials and to permit the carpet to absorb the liquid. The caustic traps were then inserted into the reactors and the reactors hooked up to the respirometer systems. The reactors were incubated in a water temperature bath maintained at 23° C. using an automatic temperature controller. The oxygen uptake by any bacteria growing in the reactors was monitored continuously and reported at 2 hour intervals.

As illustrated in FIG. 3, carpet fiber that had not been inoculated with the bacterial spore blend demonstrated only a very slight increase in oxygen uptake after about 24 hours of incubation. The oxygen uptake did not increase above this level up to 60 hours post-inoculation. These results indicate minimal bacterial growth in the control carpet sample. In contrast, the carpet fiber inoculated with the bacterial spore blend showed an increase in oxygen uptake starting 22 to 24 hours after inoculation. This increase in oxygen uptake continued up to the end of the test at 60 hours post-incubation with the oxygen intake increasing in a steady linear fashion with no leveling off of the uptake seen during the 60 hours of the test. These results indicate that the dormant bacteria are capable of germinating to become active and undergo growth in response to exposure to a suitable food source.

Example 3

To confirm that the bacterial spore blend utilized in the present invention could grow on various organic soils, plates containing materials representative of common household or soil causing organic based materials were inoculated with the bacterial spore blend. The organic based materials utilized were chocolate syrup, tomato sauce, milk, dog feces and fox urine. The growth on these soils was compared to a standard plate count broth utilized for counting colony-forming units. The plates were inoculated with dilutions of the bacterial spore blend of Example 1 to give between about 300 and 400 spores per plate and incubated at 37° C. and 50% humidity. At two days and four days post inoculation, the colony forming units (CFU) were counted and the CFU's per ml of the innoculum were calculated. As shown in FIG. 2, After two days, the bacterial preparations were growing well on the tomato sauce, chocolate syrup and dog feces, with growth almost at the level of the standard plate count broth. A minimal increase in growth on the autoclaved milk or fox urine was observed after two days, although there was some growth. After four days, the growth on all five materials was comparable, being only slightly less than the growth on the plate count broth. These results indicate that the bacterial spore blend can grow well on common organic soil, such as chocolate syrup, tomato sauce, dog feces, and fox urine.

Example 4

The bacterial spore blend was tested using respirometric studies as set out in Example 2 above to confirm that it could utilize pet waste for growth in carpets. Samples of the carpet fiber were examined for oxygen uptake using a standard respirometric study conducted using a Challenge AER100 respirometer with all samples incubated under controlled temperature conditions. The treatment reactors were 500 ml bottles. The $CO_2$ adsorption trap inserts contained 5 ml of 30% KOH (w/v) with alizarin yellow pH indicator. The sterilized traps were filled with the KOH caustic solution then inserted into the sterilized reactors using aseptic techniques. The $CO_2$ traps also contained sterilized medical cotton rolls used as wicks to increase the surface area of the caustic solution. Each reactor was provided with sufficient carpet material to yield 5 grams of carpet fiber. The organic material (i.e. dog feces, fox urine, plate count broth, etc.) was added to the reactor and the reactors autoclaved to sterilize them. The reactors were allowed to cool and 0.5 ml of the bacterial suspension containing $10^8$ spores per ml were added to the test reactors. The same volume of distilled water was added to the control reactors. The reactors were capped without the caustic traps and rolled and swirled to ensure that the water and bacterial preparations were mixed well with the organic materials and to permit the carpet to absorb the liquid. The caustic traps were then inserted into the reactors and the reactors hooked up to the respirometer systems. The reactors were incubated in a water temperature bath maintained at 23° C. using an automatic temperature controller. The oxygen uptake in the reactors was monitored continuously and reported at 2 hour intervals.

Figure 4:
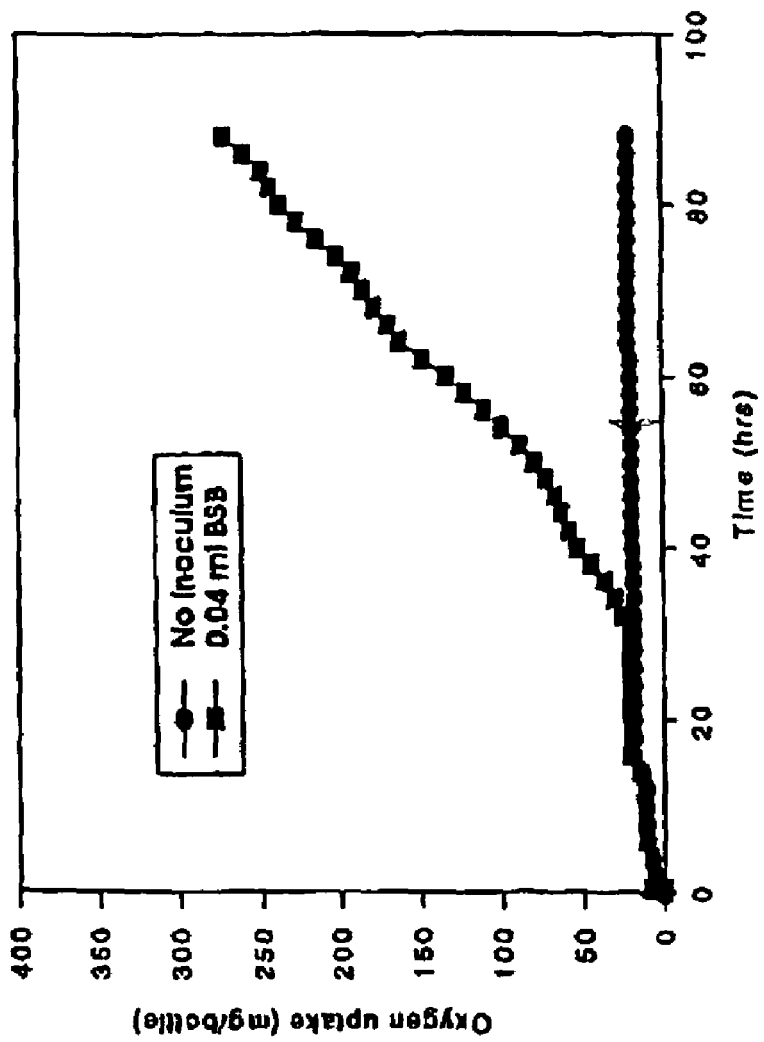
FIG. 4 is a graph illustrating the germination and growth of the bacterial spore blend on carpet containing a combination of fox urine and dog feces.

As shown in FIG. 4, the carpet sample in the control reactor with no innoculum did not have any significant increase in oxygen uptake over the 96 hours of the test. The carpet samples that had been inoculated with the bacterial spore blend started showing an increase in oxygen uptake after 32 hours post-inoculation. This increase in oxygen uptake continued to the end of the test in a linear fashion with no plateauing of the oxygen uptake observed up to 96 hours post-inoculation. This clearly shows that the bacterial spore blend associated with the carpet can become activated and undergoes growth when exposed to a common organic spill material.

Example 5

90 grams of a bacterial spore blend containing 40% *Bacillus megaterium*, 20% *Bacillus pasteurii*, 20% *Bacillus laevolacticus* and 20% *Bacillus amyloliquefaciens* was mixed with 10 grams of ZONYL 7044 fluorochemical and distilled water to yield a preparation having a concentration of about $1.0 \times 10^9$ spores per ml. To this was added either 0.1 grams of sodium bicarbonate or 0.01 of MOLSIV molecular sieve, 0.01 grams of an anti-foaming agent and sufficient acetic acid to adjust the pH to neutral. This composition was then applied to a plastic film at a concentration to give a treat rate of about $3.0 \times 10^6$ spores per square inch. The surfaces were dried and then incubated in a plate growth broth at 37 degrees, 50% humidity for 48 hours. The number of colony forming units was then determined for each sample and was found to be between $7.3 \times 10^6$ and $1.2 \times 10^7$ after 24 hours and between $1.1 \times 10^8$ and $2.3 \times 10^8$ after 48 hours. The results of this test demonstrate that the bacterial spores in the preparations were able to germinate and grow within 24-48 hours.

Example 6

To demonstrate the effectiveness of the adhering agent, dried plastic films prepared in accordance with Example 5 were introduced to flask and shaken for 24 hours in a bath to dislodge un-adhered bacteria spores. The film was removed and liquid samples taken from flask. The number of bacteria in the sample was determined by turbidity measurement, the samples were found to contain between $3.3 \times 10^4$ and $7 \times 10^4$ bacteria demonstrating that more than 97% of the bacteria spores remain associated with the surface.

The compositions and method of the present invention provide for effective odor control for surfaces, such as carpet and plastic film. The use of the bacterial preparations, particularly the sporulated forms of *Bacillus*, provide for control of odor caused by deposits of organic odor causing material on surfaces such as plastic film, carpets and other fibrous material. Once the deposit comes into contact with the bacteria, the bacteria germinate, and commence growing by feeding on the organic material as a food source. As can be observed from the above experiments with the sporulated *Bacillus*, this bacterial growth commences within about 24 and 48 hours after the bacteria encounter the deposit. In some circumstances, it may be desirable to initially mask the odor using odor masking agents or neutralize the odor using odor neutralizing agents such as sodium bicarbonate or molecular sieves until the sporulated bacteria can germinate, grow and effectively decompose the odor causing agents. Alternatively, the bacterial preparations may include suitable protease and lipase enzymes to commence the digestion of the odor causing material until the bacteria commence their growth stage and can take over the digestion of the odor causing material.

It has surprisingly been found that the odor control agent applied to the surface, particularly a carpet as described above remains effective for extended periods of time even with carpet exposed to high traffic and repeated vacuuming. It has been demonstrated that the dormant bacteria become so tightly associated with the carpet fibers that they are not easily removed when exposed to traffic or vacuuming. The use of the adhering agent such as the stain blocker and/or fluorochemical in the aqueous solution used in the application of the preparation to the carpet increases the association of the dormant bacteria with the surface, and hence increases the effective life of the treatment. It has also been demonstrated that the treatment of carpet remains after wet cleaning of the carpet. However, it is suggested that the carpet be treated with the odor controlling bacterial preparation on a routine basis such as after each wet cleaning. This can be easily accomplished after cleaning with the preparation applied to the carpet either when still wet from the cleaning or after the carpet has dried. Preferably, the preparation is applied to the carpet while still wet, worked into the carpet with a pile brush and the carpet is allowed to dry naturally.

In addition to providing for removal of potentially odor causing organic material associated with deposits on surfaces such as carpet and other fibrous material, the use of the bacterial preparations of the present invention provides other benefits. Based upon the observations from the electron micrographs, it is expected that the presence of the bacterial preparation in association with the carpet fiber and other fibrous material may result in a reduction in the presence of other bacteria and organisms which are naturally found on installed carpet and other fibrous material, both in number and population. It has also been found that the bacterial preparation associated with the carpet fiber or other fibrous material enhances the anti-stain characteristics of the carpet.

Many of the stain causing materials are organic in nature and it has been found that the bacteria can utilize such organic materials as a food source. As the bacteria consume the stain causing material, the staining properties of the compounds are reduced.

The method and compositions of the present invention are especially suitable for use with carpet as described in the specific examples set out above. These methods and compositions are also suitable for use with other fibrous material that may be susceptible to the effects of deposits of organic material. Examples of such other fibrous materials include rugs, upholstery fabrics, automotive fabrics, bedding, clothing, etc. The methods and compositions of the present invention may also be used to treat plastic films that are used in the manufacture of other products such as garbage bags, etc. Other applications may include other hard surfaces, such as ceramics, tile, walls, wood, etc.

Although various preferred embodiments of the present invention have been described herein in detail, it will be appreciated by those skilled in the art, that variations may be made thereto without departing from the spirit of the invention or the scope of the appended claims.

The embodiments of the invention in which an exclusive property or privilege is claimed are defined as follows:

1. An aqueous odor controlling bacterial composition for treating a surface, the composition selected from the group consisting of composition (A) and composition (B),
   wherein said composition (A) includes:
   (i) bacteria spores, which become active when exposed to an odor-causing organic material and which, upon activation, are capable of digesting said odor-causing organic material; and
   (ii) an adhering agent, which is at least one selected from the group consisting of a fluorochemical, an acrylic co-polymer, a styrene butadiene rubber, a nitrile rubber, a polyvinyl chloride, and a stain blocker selected from the group consisting of a sulfonated phenol formaldehyde condensate polymer, a sulfonated naphthol formaldehyde condensate polymer, and a hydrolyzed vinyl aromatic maleic anhydride polymer, in an amount sufficient to adhere said bacteria to said surface upon application of said bacterial composition thereto and to allow said bacteria to remain adhered to said surface such that said bacteria can be exposed to said odor-causing organic material and become active, and
   wherein composition (B) consists essentially of:
   (i) bacteria spores, which become active when exposed to an odor-causing organic material and which, upon activation, are capable of digesting said odor-causing organic material;
   (ii) at least one adhering agent in an amount sufficient to adhere said bacteria to said surface upon application of said bacterial composition thereto and to allow said bacteria to remain adhered to said surface such that said bacteria can be exposed to said odor-causing organic material and become active; and,
   optionally,
   (iii) at least one odor neutralizing or odor trapping agent.

2. The composition according to claim 1, comprising said composition (A).

3. The composition according to claim 1, which is said composition (B).

4. The composition according to claim 3, wherein said adhering agent is at least one selected from the group consisting of a fluorochemical, a stain blocker, an acrylic co-polymer, a styrene butadiene rubber, a nitrile rubber and a polyvinyl chloride.

5. The composition according to claim 4, wherein said adhering agent is said fluorochemical.

6. The composition according to claim 2, wherein said adhering agent is said fluorochemical.

7. The composition according to claim 2, wherein said adhering agent is said stain blocker.

8. The composition according to claim 4, wherein said adhering agent is said stain blocker.

9. The composition according to claim 8, wherein said stain blocker is selected from the group consisting of sulfonated phenol formaldehyde condensate polymer, sulfonated naphthol formaldehyde condensate polymer, and hydrolyzed vinyl aromatic male anhydride polymer.

10. The composition according to claim 2, wherein said adhering agent is said acrylic co-polymer.

11. The composition according to claim 4, wherein said adhering agent is said acrylic co-polymer.

12. The composition according to claim 2, wherein said adhering agent constitutes between 0.01 wt % and 20 wt % of said composition based upon a total weight of said composition.

13. The composition according to claim 3, wherein said adhering agent constitutes between 0.01 wt % and 20 wt % of said composition based upon a total weight of said composition.

14. The composition according to claim 12, wherein said adhering agent constitutes between 0.1 wt % and 15 wt % of said composition.

15. The composition according to claim 13, wherein said adhering agent constitutes between 0.1 wt % and 15 wt % of said composition.

16. The composition according to claim 14, wherein said adhering agent constitutes between 5 wt % and 10 wt % of said composition.

17. The composition according to claim 15, wherein said adhering agent constitutes between 5 wt % and 10 wt % of said composition.

18. The composition according to claim 2, further comprising at least one odor neutralizing or odor trapping agent.

19. The composition according to claim 3, comprising said at least one odor neutralizing or odor trapping agent.

20. The composition according to claim 18, wherein said odor neutralizing or odor trapping agent is sodium bicarbonate or molecular sieves.

21. The composition according to claim 19, wherein said odor neutralizing or odor trapping agent is sodium bicarbonate or molecular sieves.

22. The composition according to claim 2, wherein said bacteria are of the genus *Bacillus*.

23. The composition according to claim 3, wherein said bacteria are of the genus *Bacillus*.

24. The composition according to claim 22, wherein said bacteria of the genus *Bacillus* is one or more strains selected from the group of bacterial species consisting of *Bacillus megaterium, Bacillus pasteurii, Bacillus laevolacticus* and *Bacillus amyloliquefaciens*.

25. The composition according to claim 23, wherein said bacteria of the genus *Bacillus* is one or more strains selected from the group of bacterial species consisting of *Bacillus megaterium, Bacillus pasteurii, Bacillus laevolacticus* and *Bacillus amyloliquefaciens*.

* * * * *